(12) United States Patent
Yamada et al.

(10) Patent No.: US 12,241,369 B2
(45) Date of Patent: Mar. 4, 2025

(54) SYSTEMS AND METHODS FOR PERFORMING LITHOLOGICAL CLASSIFICATION OF CUTTINGS BASED ON CALIBRATED PHOTOGRAPHS OF ROCK PARTICLES

(71) Applicant: Schlumberger Technology Corporation, Sugar Land, TX (US)

(72) Inventors: Tetsushi Yamada, Cambridge, MA (US); Simone Di Santo, Dhahran (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 555 days.

(21) Appl. No.: 17/647,412

(22) Filed: Jan. 7, 2022

(65) Prior Publication Data

US 2023/0220770 A1    Jul. 13, 2023

(51) Int. Cl.
*E21B 49/00* (2006.01)
*G01N 15/0227* (2024.01)
(Continued)

(52) U.S. Cl.
CPC ....... *E21B 49/005* (2013.01); *G01N 15/0227* (2013.01); *G01N 15/1433* (2024.01);
(Continued)

(58) Field of Classification Search
CPC ........ G06V 10/40; G06V 10/54; G06V 10/56; G06V 10/764; E21B 49/005; G01V 20/00
See application file for complete search history.

(56) References Cited

U.S. PATENT DOCUMENTS

| | | | |
|---|---|---|---|
| 7,936,374 B2 * | 5/2011 | Cutler | H04N 23/90 348/211.3 |
| 9,412,023 B1 | 8/2016 | Hurley | |

(Continued)

FOREIGN PATENT DOCUMENTS

| | | |
|---|---|---|
| CN | 111141698 A | 5/2020 |
| EP | 3896496 A1 | 10/2021 |
| WO | 2019167030 A1 | 9/2019 |

OTHER PUBLICATIONS

Becerra et al., Generating a labeled data set to train machine learning algorithms for lithologic classification of drill cuttings, Special section: Machine learning for image-based geologic interpretation, May 2022, pp. SE85-SE100, doi.org/10.1190/INT-2021-0194.1.*

(Continued)

*Primary Examiner* — Guillermo M Rivera-Martinez
(74) *Attorney, Agent, or Firm* — Jeffrey D. Frantz

(57) ABSTRACT

Systems and methods are configured to receive one or more photographs depicting a plurality of cuttings, to identify one or more individual cuttings of the plurality of cuttings depicted in the one or more photographs, to extract morphological, color, texture, grain size, and grain distribution data from each individual cutting of the one or more individual cuttings, to perform lithological classification of the one or more individual cuttings at a plurality of hierarchical levels based at least in part on the extracted morphological, color, texture, grain size, and grain distribution data or based at least in part on features directly extracted from the one or more individual cuttings that represent the morphological, color, texture, grain size, and grain distribution data, and to present a consolidated results summary of the (Continued)

lithological classification of the one or more individual cuttings at the plurality of hierarchical levels via the analysis and control system.

20 Claims, 12 Drawing Sheets

(51) Int. Cl.
    *G01N 15/1433*     (2024.01)
    *G01N 33/24*     (2006.01)
    *G06T 7/40*     (2017.01)
    *E21B 21/06*     (2006.01)
    *E21B 44/00*     (2006.01)

(52) U.S. Cl.
    CPC ............... *G01N 33/24* (2013.01); *G06T 7/40* (2013.01); *E21B 21/066* (2013.01); *E21B 44/00* (2013.01); *E21B 2200/20* (2020.05); *G06T 2207/10004* (2013.01)

(56) References Cited

U.S. PATENT DOCUMENTS

| | | | | |
|---|---|---|---|---|
| 9,507,047 | B1* | 11/2016 | Dvorkin | G01V 5/101 |
| 9,652,684 | B2 | 5/2017 | Keskes et al. | |
| 10,927,671 | B1* | 2/2021 | Tonner | E21B 21/01 |
| 11,188,794 | B2 | 11/2021 | Yao et al. | |
| 11,719,089 | B2* | 8/2023 | Affleck | G06N 3/02 |
| | | | | 702/6 |
| 2005/0276513 | A1 | 12/2005 | Ojanen | |
| 2010/0128932 | A1* | 5/2010 | Dvorkin | G01N 23/046 |
| | | | | 382/109 |
| 2012/0123756 | A1 | 5/2012 | Wang | |
| 2013/0073207 | A1* | 3/2013 | Ganz | G01N 33/24 |
| | | | | 73/152.05 |
| 2013/0120763 | A1 | 5/2013 | Grenet | |
| 2013/0259190 | A1* | 10/2013 | Walls | G01N 23/046 |
| | | | | 382/109 |
| 2014/0046628 | A1 | 2/2014 | Ligneul et al. | |
| 2015/0043787 | A1* | 2/2015 | Fredrich | G06T 7/11 |
| | | | | 382/109 |
| 2016/0370274 | A1* | 12/2016 | Rowe | G01N 15/1433 |
| 2017/0085860 | A1 | 3/2017 | Zhang | |
| 2018/0101962 | A1 | 4/2018 | Takizawa | |
| 2018/0180524 | A1* | 6/2018 | François | G06V 10/50 |
| 2019/0212272 | A1* | 7/2019 | Scoullar | G01N 21/85 |
| 2019/0338637 | A1* | 11/2019 | Francois | E21B 49/08 |
| 2020/0025667 | A1* | 1/2020 | Allo | G01N 15/088 |
| 2020/0143205 | A1 | 5/2020 | Yao | |
| 2020/0150307 | A1 | 5/2020 | Myers | |
| 2020/0157929 | A1* | 5/2020 | Torrione | E21B 44/00 |
| 2021/0041588 | A1* | 2/2021 | Chen | G01V 1/307 |
| 2021/0254457 | A1 | 8/2021 | Anifowose | |
| 2021/0312674 | A1 | 10/2021 | Abrol et al. | |
| 2021/0319257 | A1* | 10/2021 | Francois | G01N 15/088 |
| 2023/0184992 | A1* | 6/2023 | Albahrani | E21B 49/005 |
| | | | | 175/24 |
| 2023/0220761 | A1 | 7/2023 | Yamada et al. | |
| 2023/0351580 | A1 | 11/2023 | Di Santo | |
| 2024/0054766 | A1* | 2/2024 | Yu | G06V 10/14 |

OTHER PUBLICATIONS

Abbireddy, C.O.R. et al., "A method of estimating the form of fine particulates", Geotechnique, 2009, 59(6), pp. 503-511.

Barrett, P. J. "The shape of rock particles, a critical review", Sedimentology, 1980, 27, pp. 291-303.

Caicedo, J. C. et al., "Nucleus segmentation across imaging experiments: the 2018 Data Science Bowl", Nature Methods, 2019, 16, pp. 1247-1253.

Dunlop, H. et al., "Multi-scale Features for Detection and Segmentation of Rocks in Mars Images", 2007, 10.1109/CVPR.2007.383257, 7 pages.

Feng, L. et al., "Robust Nucleus Detection with Partially Labeled Exemplars", IEEE Access (7), 2019, pp. 162169-162178.

Gaetano, R. et al., "Hierarchical Texture-Based Segmentation of Multiresolution Remote-Sensing Images", IEEE Transactions on Geoscience and Remote Sensing, 2009, 47(7), pp. 2129-2141.

He, K. et al., "Mask R-CNN", Computer Vision (ICCV), IEEE International Conference on Computer Vision, 2017, pp. 2980-2988.

He, K. et al., "Deep Residual Learning for Image Recognition", 2016 IEEE International Conference on Computer Vision, 2016, pp. 770-778.

Huo, F. et al., "Novel lithology identification method for drilling cuttings under PDC bit condition", Journal of Petroleum Science and Engineering, 2021, 205, 15 pages.

Jung, H. et al., "An automatic nuclei segmentation method based on deep convolutional neural networks for histopathology images", BMC Biomedical Engineering, 2019, 1:24, 12 pages.

Lin, T. Y. et al., "Microsoft COCO: Common Objects in Context", ECCV 2014: Computer Vision—ECCV 2014, pp. 740-755.

Lin, T.-Y. et al., "Feature Pyramid Networks for Object Detection", Computer Vision and Pattern Recognition (CVPR), IEEE International Conference on Computer Vision 2017, pp. 936-944.

Rahmani, H. et al., "Automated segmentation of gravel particles from depth images of gravel-soil mixtures", Compute and Geosciences, 2019, 128, pp. 1-10.

Ravali, K. et al., "Graph-Based High Resolution Satellite Image Segmentation for Object Recognition", The International Archives of the Photogrammetry, Remote Sensing and Spatial Information Sciences, 2014, vol. XL-8, pp. 913-917.

Sanxo-Scope HD U4 Express: Industrial Microscope downloaded from the internt at [https://sanxo.eu/sanxo-scope-hd-u4-express-industrial-microscope/] on Apr. 21, 2022, 8 pages.

Shi, J. et al., "Normalized Cuts and Image Segmentation", IEEE Transactions on Pattern Analysis and Machine Intelligence, 2000, 22(8), pp. 888-905.

Thurley, M. J., "Automated Image Segmentation and Analysis of Rock Piles in an Open-Pit Mine", International Conference on Digital Image Computing: Techniques and Applications (DICTA), 2013, 10.1109/DICTA.2013.6691484, 8 Pages.

Ting, G. et al., "Rock Particle Image Segmentation Based on Improved Normalized Cut", International Journal of Control and Automation, 2017, 10(4), pp. 271-286.

Wang, W., "Rock Particle Image Segmentation and Systems", in Pattern Recognition Techniques, Technology and Applications, Book edited by: Peng-Yeng Yin, Nov. 2008, I-Tech, Vienna, Austria, 10.5772/6242, 30 pages.

Wikipedia "Semi Supervised Learning" downloaded from the internet at [https://en.wikipedia.org/wiki/Semi-supervised_learning] retrieved on Apr. 21, 2022, 7 pages.

Wikipedia "Transfer Learning" downloaded from the internet at [https://en.wikipedia.org/wiki/Transfer_learning] retrieved on Apr. 21, 2022, 5 pages.

Wikipedia "Run-length encoding", downloaded from the internet at [https://en.wikipedia.org/wiki/Run-length_encoding] retrieved on Apr. 21, 2022, 3 pages.

"Pytorch/vision" downloaded from the internet at [https://github.com/pytorch/vision] retrieved on Apr. 21, 2022, 6 pages.

"Mongoose Pro Dynamic dual-motion shaker", retrieved from the internet: [https://www.slb.com/drilling/drilling-fluids-and-well-cementing/solids-control/shale-shakers/mongoose-pro-shale-shaker] Apr. 19, 2022, 9 pages.

Search Report and Written Opinion of International Patent Application No. PCT/US2021/044883 dated Nov. 16, 2021, 10 pages.

Using colorcheck. Imatest, Retrieved Mar. 4, 2022, from https://www.imatest.com/docs/colorcheck/, 26 pages.

Sharpness: What is it and how it is measured. Imatest, Retrieved Mar. 4, 2022, from https://www.imatest.com/docs/sharpness/, 17 pages.

Beard et al., Influence of texture on porosity and permeability of unconsolidated sand. American Association of Petroleum Geologists Bulletin, vol. 27, No. 2, Feb. 1973, p. 349-369.

(56) References Cited

OTHER PUBLICATIONS

Ameen et al., The function of fractures and in-situ stresses in the Khuff reservoir performance, onshore fields, Saudi Arabia, American Association of Petroleum Geologists Bulletin, vol. 94, No. 1, Jan. 2010, pp. 27-60.
Blaschke et al., Object-Based Image Analysis. Springer. p. 37. ISBN: 978-3-540-77057-2, 2008, 30 pages.
International Preliminary Report on Patentability issued in the PCT Application No. PCT/US2021/044883 mailed Feb. 16, 2023, 7 pages.
International Search Report and Written Opinion issued in PCT Application No. PCT/US2022/053454 dated Apr. 25, 2023, 10 pages.
International Search Report and Written Opinion issued in PCT Application No. PCT/US2022/060240 dated Apr. 28, 2023, 10 pages.
Liang, Z. et al., "A particle shape extraction and evaluation method using a deep convolutional neural network and digital image processing", Powder Technology, 2019, 353, pp. 156-170.
International Search Report and Written Opinion issued in PCT Application No. PCT/US2023/015998 dated Jul. 11, 2023, 11 pages.
International Search Report and Written Opinion issued in PCT Application No. PCT/US2023/070658 dated Nov. 8, 2023, 12 pages.
Office Action issued in U.S. Appl. No. 17/647,407 dated Jun. 25, 2024, 22 pages.
International Preliminary Report on Patentability issued in International Patent application PCT/US2023/060240, dated Jun. 20, 2024, 6 pages.
International Preliminary Report on Patentability issued in International Patent application PCT/US2022/053454, dated Jun. 20, 2024, 6 pages.

* cited by examiner

SYSTEMS AND METHODS FOR PERFORMING LITHOLOGICAL CLASSIFICATION OF CUTTINGS BASED ON CALIBRATED PHOTOGRAPHS OF ROCK PARTICLES

BACKGROUND

The present disclosure generally relates to systems and methods for measuring physical lithological features based on calibrated photographs of rock particles and, more specifically, to the analysis of individual rock particles that are identified in the calibrated photographs of the rock particles.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Automatically detecting rock particles has wide industry and scientific applications including, but not limited to, space exploration, mining, civil engineering, geothermal, and oil and gas. Many research projects have been conducted for such task for several decades. The data typically comes from imaging systems that produce digital photos or three-dimensional (3D) images from a laser scanner. Rock particles are usually a fundamental unit of domain-specific post-processing analysis. Once particles are detected and segmented, they can be used to compute the properties of particles such as size, shapes, textures, and categories based on those properties to answer domain-specific questions.

In oil and gas, geothermal, as well as scientific exploration applications, rock particles are naturally produced during drilling activities. Those particles are called rock cuttings and are one of the highest available and lowest cost data sources for understanding and characterizing the subsurface rock properties. As such, there is a strong industry need to automatically analyze rock cuttings to reduce human cost and shorten the turnaround time of the interpretation.

However, particle segmentation is not a simple task for multiple reasons. For example, it is the most important and hardest part of pattern recognition for rock particles. Rock particles usually have varying morphologies, texture, and colors. When the scene is captured by a sensor in an imaging system, artefacts, such as shadow and light reflection on the surface of the particle, may be introduced in the image. Furthermore, when the particles are piled on or touching each other, the segmentation becomes even more difficult. In such cases, the limits of particles can be very subtle even for a human's eye, depending on type of rock and other factors such as lighting conditions. However, facing such situations is almost inevitable in most industry applications. In addition, separating particles before capturing the scene often introduces additional human interventions, which is not desirable.

In the past, a variety of segmentation methods have been explored such as the watershed transform and normalized cuts. The watershed transform is especially popular for its simplicity, efficiency, and availability of the computation library such as OpenCV. It is often proceeded by morphological operations and followed by refinements. However, the result is highly dependent on the hyper-parameters, and it often suffers from under-segmentation or over-segmentation. In addition, it is generally not easy to design the pre-processing parts so that the segmentation works when the sizes of the objects are not uniform. Despite these prior efforts, automatic segmentation has been far from accurate.

SUMMARY

A summary of certain embodiments described herein is set forth below. It should be understood that these aspects are presented merely to provide the reader with a brief summary of these certain embodiments and that these aspects are not intended to limit the scope of this disclosure.

Certain embodiments of the present disclosure include a method that includes calibrating, via an analysis and control system, one or more photographs that depict a plurality of cuttings. The method also includes identifying, via the analysis and control system, one or more individual cuttings of the plurality of cuttings depicted in the one or more calibrated photographs. The method further includes extracting, via the analysis and control system, morphological, color, texture, grain size, and grain distribution data from each individual cutting of the one or more individual cuttings. In addition, the method includes performing, via the analysis and control system, lithological classification of the one or more individual cuttings at a plurality of hierarchical levels based at least in part on the extracted morphological, color, texture, grain size, and grain distribution data or based at least in part on features directly extracted from the one or more individual cuttings that represent the morphological, color, texture, grain size, and grain distribution data. The method also includes presenting, via the analysis and control system, a consolidated results summary of the lithological classification of the one or more individual cuttings at the plurality of hierarchical levels via the analysis and control system.

Certain embodiments of the present disclosure also include an analysis and control system that is configured to calibrate one or more photographs that depict a plurality of cuttings. The analysis and control system is also configured to identify one or more individual cuttings of the plurality of cuttings depicted in the one or more calibrated photographs. The analysis and control system is further configured to extract morphological, color, texture, grain size, and grain distribution data from each individual cutting of the one or more individual cuttings. In addition, the analysis and control system is configured to perform lithological classification of the one or more individual cuttings at a plurality of hierarchical levels based at least in part on the extracted morphological, color, texture, grain size, and grain distribution data or based at least in part on features directly extracted from the one or more individual cuttings that represent the morphological, color, texture, grain size, and grain distribution data. The analysis and control system is also configured to present a consolidated results summary of the lithological classification of the one or more individual cuttings at the plurality of hierarchical levels via the analysis and control system.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings, in which.

DETAILED DESCRIPTION

Figure 1:
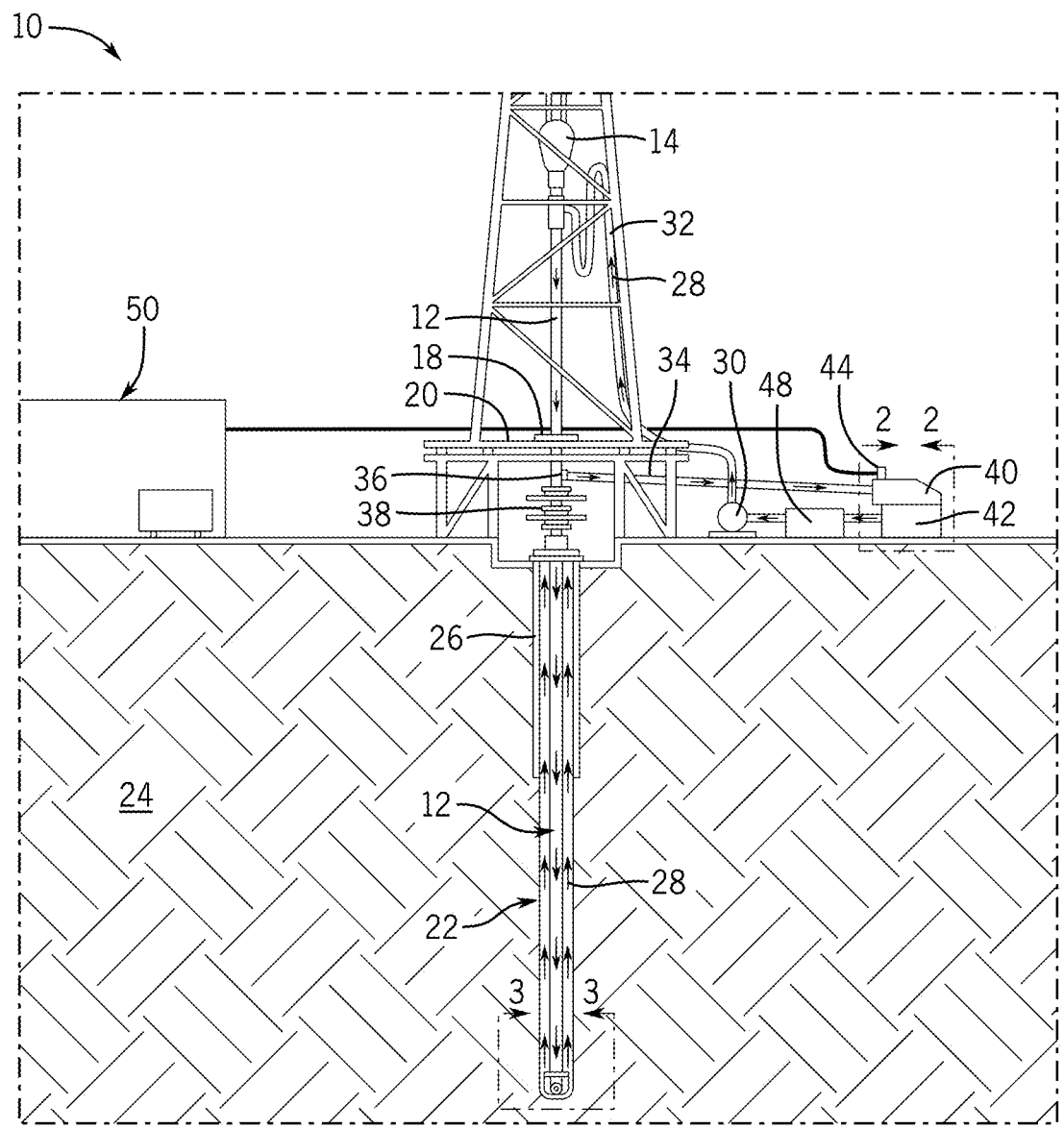
FIG. 1 illustrates a drilling operation, in accordance with embodiments of the present disclosure.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As used herein, the terms "connect," "connection," "connected," "in connection with," and "connecting" are used to mean "in direct connection with" or "in connection with via one or more elements"; and the term "set" is used to mean "one element" or "more than one element." Further, the terms "couple," "coupling," "coupled," "coupled together," and "coupled with" are used to mean "directly coupled together" or "coupled together via one or more elements."

In addition, as used herein, the terms "real time", "real-time", or "substantially real time" may be used interchangeably and are intended to describe operations (e.g., computing operations) that are performed without any human-perceivable interruption between operations. For example, as used herein, data relating to the systems described herein may be collected, transmitted, and/or used in control computations in "substantially real time" such that data readings, data transfers, and/or data processing steps occur once every second, once every 0.1 second, once every 0.01 second, or even more frequent, during operations of the systems (e.g., while the systems are operating). In addition, as used herein, the terms "continuous", "continuously", or "continually" are intended to describe operations that are performed without any significant interruption. For example, as used herein, control commands may be transmitted to certain equipment every five minutes, every minute, every 30 seconds, every 15 seconds, every 10 seconds, every 5 seconds, or even more often, such that operating parameters of the equipment may be adjusted without any significant interruption to the closed-loop control of the equipment. In addition, as used herein, the terms "automatic", "automated", "autonomous", and so forth, are intended to describe operations that are performed are caused to be performed, for example, by a computing system (i.e., solely by the computing system, without human intervention). Indeed, although certain operations described herein may not be explicitly described as being performed continuously and/or automatically in substantially real time during operation of the computing system and/or equipment controlled by the computing system, it will be appreciated that these operations may, in fact, be performed continuously and/or automatically in substantially real time during operation of the computing system and/or equipment controlled by the computing system to improve the functionality of the computing system (e.g., by not requiring human intervention, thereby facilitating faster operational decision-making, as well as improving the accuracy of the operational decision-making by, for example, eliminating the potential for human error), as described in greater detail herein.

As described above, whenever a drilling process is involved in an activity, rock cuttings are produced and are always available at the wellsite. Currently, cuttings are generally under-utilized for the subsurface characterization by geoscientists and reservoir engineers in the oil and gas industry. When these rock cuttings are observed and interpreted by human eyes, it is extremely interpreter-dependent and relatively time consuming as well as physically labor intensive. To fill this gap, there is a strong industry interest in automating the process of cuttings analysis in the industry. To that end, the embodiments described herein provide a domain-based image analysis workflow that includes multiple computational modules to automatically extract relevant geological information from rock cuttings. As used herein, the terms "image", "digital image", "photograph", and "photo" are intended to be used interchangeably. In addition, although described herein as systems and methods for analyzing photos of drill bit cuttings, it will be appreciated that the embodiments described herein may be capable of analyzing photos of other types of rock particles, such as other types of cuttings, cavings, and so forth.

FIG. 1 illustrates a drilling operation 10 in accordance with the embodiments described herein. As illustrated, in certain embodiments, a drill string 12 may be suspended at an upper end by a kelly 12 and a traveling block 14 and terminated at a lower end by a drill bit 16. The drill string 12 and the drill bit 16 are rotated by a rotary table 18 on a driller floor 20, thereby drilling a borehole 22 into earth formation 24, where a portion of the borehole 22 may be cased by a casing 26. As illustrated, in certain embodiments, drilling fluid or drilling "mud" 28 may be pumped by a mud pump 30 into the upper end of the hollow drill string 12 through a connecting mud line 32. From there, the drilling fluid 28 may be pumped downward through the drill string 12, exiting the drill string 12 through opening in the drill bit 16, and returning to the surface by way of an annulus formed between the wall of the borehole 22 and an outer diameter of the drill string 12. Once at the surface, the drilling fluid 28 may return through a return flow line 34, for example, via a bell nipple 36. As illustrated, in certain embodiments, a blowout preventer 38 may be used to prevent blowouts from occurring in the drilling operation 10.

Figure 3:
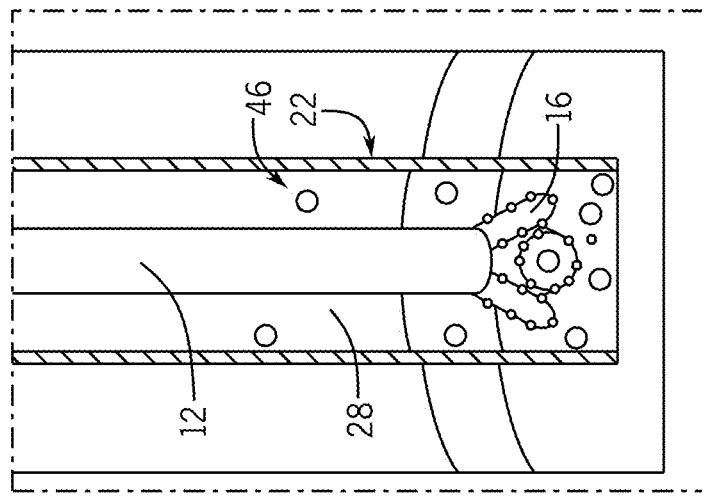
FIG. 3 illustrates how drill bit cuttings may be created by the drill bit, in accordance with embodiments of the present disclosure.
Figure 2:
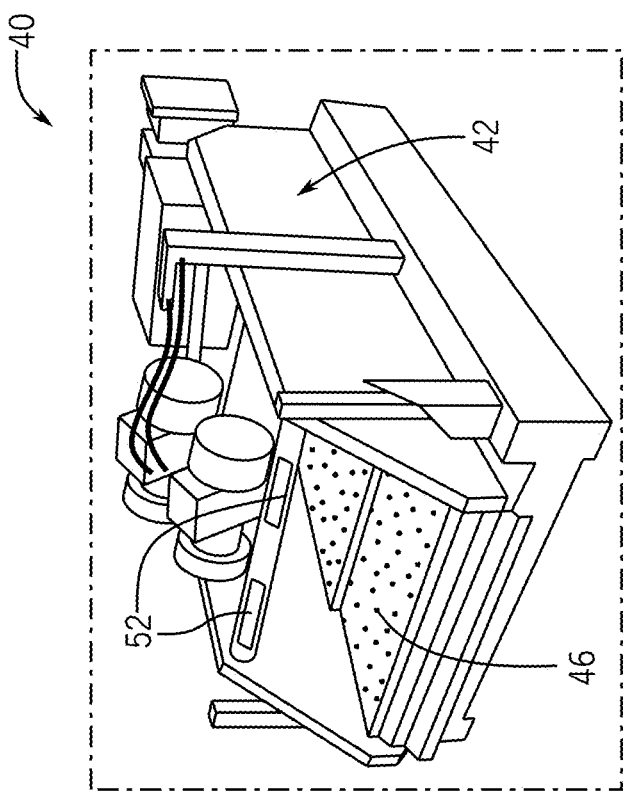
FIG. 2 illustrates drill bit cuttings that have been removed from drilling fluid, in accordance with embodiments of the present disclosure.

As illustrated in FIG. 1, drill bit cuttings that are formed by the drill bit 16 crushing rocks in the formation 24 may typically be removed from the returned drilling fluid 28 by a shale shaker 40 in the return flow line 34 such that the drilling fluid 28 may be reused for injection, where the shale shaker 40 includes a shaker pit 42 and a gas trap 44. FIG. 2 illustrates drill bit cuttings 46 that have been removed from the drilling fluid 28 in the shaker pit 42 of the shale shaker 40 before the drilling fluid 28 is delivered to a mud pit 48 from which the mud pump 30 may draw the drilling fluid 28, as illustrated in FIG. 1. In addition, FIG. 3 illustrates how drill bit cuttings 46 may be created by the drill bit 16, and then flow back up within the drilling fluid 28 through an annulus formed between the wall of the borehole 22 and an outer diameter of the drill string 12.

In addition, as illustrated in FIG. 1, in certain embodiments, an analysis and control system 50 (e.g., a mud logging unit) may be used to control the drilling operation 10, as well as provide analysis of the drill bit cuttings 46, as described in greater detail herein. In particular, in certain embodiments, the analysis and control system 50 may be configured to automatically analyze photos of the drill bit cuttings 46 that are automatically captured by one or more cameras 52 during performance of the drilling operation 10 illustrated in FIG. 1, as described in greater detail herein. As illustrated in FIG. 2, in certain embodiments, the one or more cameras 52 may be directed associated with (e.g., directly attached to or disposed adjacent to or in close proximity to) the shale shaker 40. However, in other embodiments, the one or more cameras 52 may be other types of cameras not directly associated with the shale shaker 40.

Figure 4:
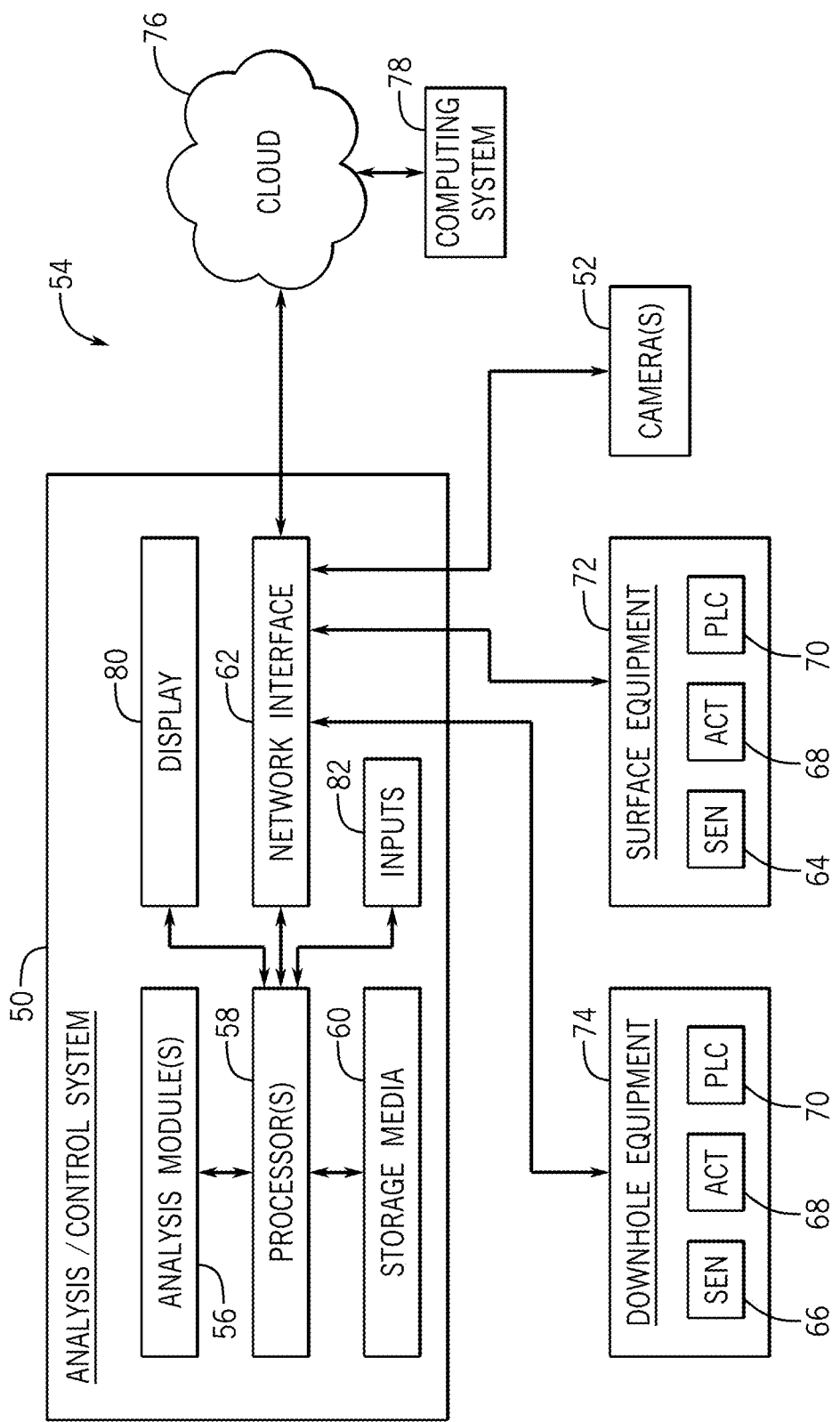
FIG. 4 illustrates a system that includes an analysis and control system to monitor and control the drilling operation 10 of FIG. 1, in accordance with embodiments of the present disclosure.

FIG. 4 illustrates a system 54 that includes an analysis and control system 50 to monitor and control the drilling operation 10 of FIG. 1, as described in greater detail herein. In certain embodiments, the analysis and control system 50 may include one or more analysis modules 56 (e.g., a program of processor executable instructions and associated data) that may be configured to perform various functions of the embodiments described herein including, but not limited to, utilizing certain analysis algorithms to analyze photos of drill but cuttings 46 that are captured by one or more cameras 52, as described in greater detail herein. In certain embodiments, to perform these various functions, an analysis module 56 executes on one or more processors 58 of the analysis and control system 50, which may be connected to one or more storage media 60 of the analysis and control system 50. Indeed, in certain embodiments, the one or more analysis modules 56 may be stored in the one or more storage media 60.

In certain embodiments, the one or more processors 58 may include a microprocessor, a microcontroller, a processor module or subsystem, a programmable integrated circuit, a programmable gate array, a digital signal processor (DSP), or another control or computing device. In certain embodiments, the one or more storage media 60 may be implemented as one or more non-transitory computer-readable or machine-readable storage media. In certain embodiments, the one or more storage media 60 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the processor-executable instructions and associated data of the analysis module(s) 56 may be provided on one computer-readable or machine-readable storage medium of the storage media 60 or, alternatively, may be provided on multiple computer-readable or machine-readable storage media distributed in a large system having possibly plural nodes. Such computer-readable or machine-readable storage medium or media are considered to be part of an article (or article of manufacture), which may refer to any manufactured single component or multiple components. In certain embodiments, the one or more storage media 60 may be located either in the machine running the machine-readable instructions, or may be located at a remote site from which machine-readable instructions may be downloaded over a network for execution.

In certain embodiments, the processor(s) 58 may be connected to a network interface 62 of the analysis and control system 50 to allow the analysis and control system 50 to communicate with various surface sensors 64 (Internet of Things (IoT) sensors, gauges, and so forth) and/or downhole sensors 66 described herein, as well as communicate with actuators 68 and/or PLCs 70 of surface equipment 72 and/or of downhole equipment 74 for the purpose of monitoring and/or controlling operation of the drilling operation 10, as described in greater detail herein. In addition, in certain embodiments, the network interface 62 may also facilitate the analysis and control system 50 to communicate with one or more cameras 52, as described in greater detail herein. In certain embodiments, the network interface 62 may also facilitate the analysis and control system 50 to communicate data to a cloud-based service 76 (or other wired and/or wireless communication network) to, for example, archive the data or to enable external computing systems 78 (e.g., cloud-based computing systems, in certain embodiments) to access the data and/or to remotely interact with the analysis and control system 50. For example, in certain embodiments, some or all of the analysis modules 56 described in greater detail herein may be executed via cloud and edge deployments.

In certain embodiments, the analysis and control system 50 may include a display 80 configured to display a graphical user interface to present results on the analysis described herein. In addition, in certain embodiments, the graphical user interface may present other information to operators of the equipment 72, 74. For example, the graphical user interface may include a dashboard configured to present visual information to the operators. In certain embodiments, the dashboard may show live (e.g., real-time) data as well as the results of the analysis described herein. In addition, in certain embodiments, the analysis and control system 50 may include one or more input devices 82 configured to enable the operators to, for example, provide commands to the equipment 72, 74 described herein. In addition, in certain embodiments, the display 80 may include a touch screen interface configured to receive inputs from operators.

It should be appreciated that the system 54 illustrated in FIG. 4 is only exemplary, and that the system 54 may have more or fewer components than shown, may combine additional components not depicted in the embodiment of FIG. 4, and/or the system 54 may have a different configuration or arrangement of the components depicted in FIG. 4. In addition, the various components illustrated in FIG. 4 may be implemented in hardware, software, or a combination of both hardware and software, including one or more signal processing and/or application specific integrated circuits. Furthermore, the operations of the system 52 as described herein may be implemented by running one or more functional modules in an information processing apparatus such as application specific chips, such as application-specific integrated circuits (ASICs), field-programmable gate arrays (FPGAs), programmable logic devices (PLDs), systems on a chip (SOCs), or other appropriate devices. These modules, combinations of these modules, and/or their combination with hardware are all included within the scope of the embodiments described herein.

Figure 5:
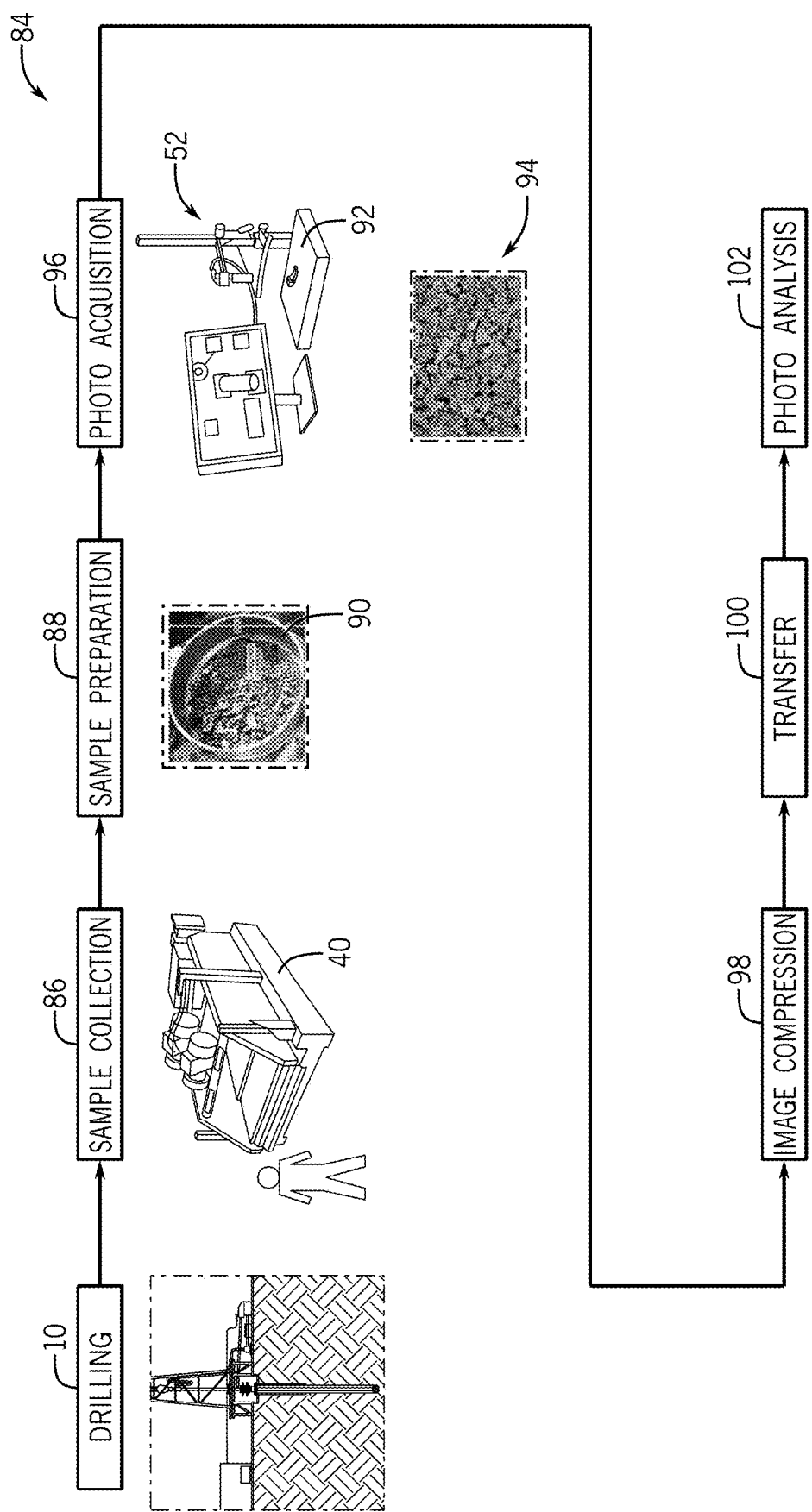
FIG. 5 illustrates a cuttings analysis procedure that may be performed by the analysis and control system of FIG. 4, in accordance with embodiments of the present disclosure.

In conventional systems, drill bit cuttings 46 are analyzed by mud loggers in a mud logging unit. These conventional systems are generally human-dependent. The embodiments described herein enhance the analysis of such drill bit cuttings 46. FIG. 5 illustrates a cuttings analysis procedure 84 that may be performed by the analysis and control system 50 of FIG. 4. As illustrated in FIG. 5, the cuttings analysis procedure 84 begins with a drilling operation 10 that generates rock particles (e.g., that include the drill bit cuttings 46 described above). Then, the rock particles are collected, for example, from a shale shaker 40, as described with respect to FIG. 2 (e.g., sample collection 86).

Then, in certain embodiments, the rock particles may be prepared for analysis by, for example, drying the rock particles in an oven for analysis (e.g., sample preparation 88). In addition, in certain embodiments, the sample preparation 88 may include sieving the rock particles using one or more meshes 90 to select cuttings 46 that fall in certain ranges of sizes. In certain embodiments, the sizes of the meshes 90 may be in a range of between 0.25 millimeters (mm) and 3.0 mm and may be approximately 0.25 mm, approximately 0.50 mm, approximately 0.75 mm, approximately 1.0 mm, approximately 1.25 mm, approximately 1.50 mm, approximately 1.75 mm, approximately 2.0 mm, approximately 2.25 mm, approximately 2.50 mm, approximately 2.75 mm, or approximately 3.0 mm. It will be appreciated that consecutive meshes 90 through which the rock particles may be sieved may begin with larger meshes 90 followed by progressively smaller meshes 90 such that larger cuttings 46 are sieved sooner and smaller cuttings 46 are sieved later until such point where the sieved rock particles are so fine that they are no longer considered cuttings 46 per se. It will also be appreciated that the size of a particle cutting 46 is the smallest axis of the cutting 46 when the cutting 46 is approximated as an ellipsoid. In certain embodiments, the sample preparation 88 may include placing the sieved cuttings 46 in a tray 92 having a relatively vivid background color (e.g., pure magenta (e.g., with RGB values of 255, 0, 255), pure blue (e.g., with RGB values of 0, 0, 255), pure green (e.g., with RGB values of 0, 255, 0), and so forth). In general, such colors do not exist in nature and, accordingly, help instance segmentation models avoid detecting the background of the tray 92 as part of the instance. In certain situations, the tray 92 may be prepared by a human, so the distribution of the cuttings 46 is often random. For example, the cuttings 46 may be touching or piled in some areas on the tray 92 and may be sparsely distributed in other areas.

Then, in certain embodiments, the tray 92 may be placed in front of a camera 52 and a photo 94 of the cuttings 46 may be taken (e.g., photo acquisition 96). As described in greater detail herein, in certain embodiments, during the photo acquisition 96, illumination, color, and resolution of the photo 94 are calibrated and standardized in order to obtain quantitative and reliable measurements of pixel values between photos 94. For example, in certain embodiments, color/illumination calibration is obtained by using colorimetry algorithms against previously analyzed photos 94 and a current photo of interest 94, while resolution calibration may be based on lens focal length, focal distance, and sensor size/resolution for the current photo 94 of interest as compared to that of previously analyzed photos 94. All of these parameters may vary, but the final image is "calibrated" and the same objects will be digitalized with reasonably near values. Pixel values and size are, therefore, treated as effective measurements of the particle rather than mere representation. The embodiments described herein enable the creation of such calibrated and error-assessed input images 94. Without such calibration, final object classification would vary because of the acquisition rather than because of any real-world difference.

Then, in certain embodiments, the photo 94 of the cuttings 46 may be compressed for easier transfer (e.g., image compression 98). In particular, well sites are quite often in relatively remote locations where the available network bandwidth may be relatively slow. Accordingly, compressing the photos 94 of cuttings 46 may facilitate transfer of the photos 94. It will be appreciated that compressing the photos 94 of cuttings 46 may not be as beneficial if there is higher bandwidth at the well site (e.g., when the well site has cable internet access). Then, in certain embodiments, the photo 94 of the cuttings 46 may be transferred 100, for example, to the analysis and control system 50 and/or the computing system 78 illustrated in FIG. 4 for analysis, as described in greater detail herein. Then, in certain embodiments, analysis of the photo 94 of the cuttings 46 (e.g., photo analysis 102) may include extraction of geologically meaningful information relating to the cuttings 46 from the photo 94, as described in greater detail herein.

The embodiments described herein determine measurements from photos 94 of cuttings 46 that relate to lithology of the formation 24 from which the cuttings 46 are generated based on lithology geological scientific definitions. In general, the lithology of a rock unit is a description of its physical characteristics visible at an outcropping, in hand or core samples, or with low magnification microscopy. Such physical characteristics include, but are not limited to, color, texture, grain size, and composition. Lithology may refer to either a detailed description of these physical characteristics, or a summary of the gross physical character of a rock. Examples of lithologies in the second sense include sandstone, slate, basalt, limestone, and so forth. As such, color, texture, and grain size are physical characteristics of a lithology, and the workflows described herein illustrate how these physical characteristics may be measured, extracted, and consolidated to obtain automated lithological image recognition. The embodiments described herein apply to analysis of prepared cuttings 46, regardless of the particular methods used to achieve the sample preparation 88 described with respect to FIG. 5.

Figure 6:
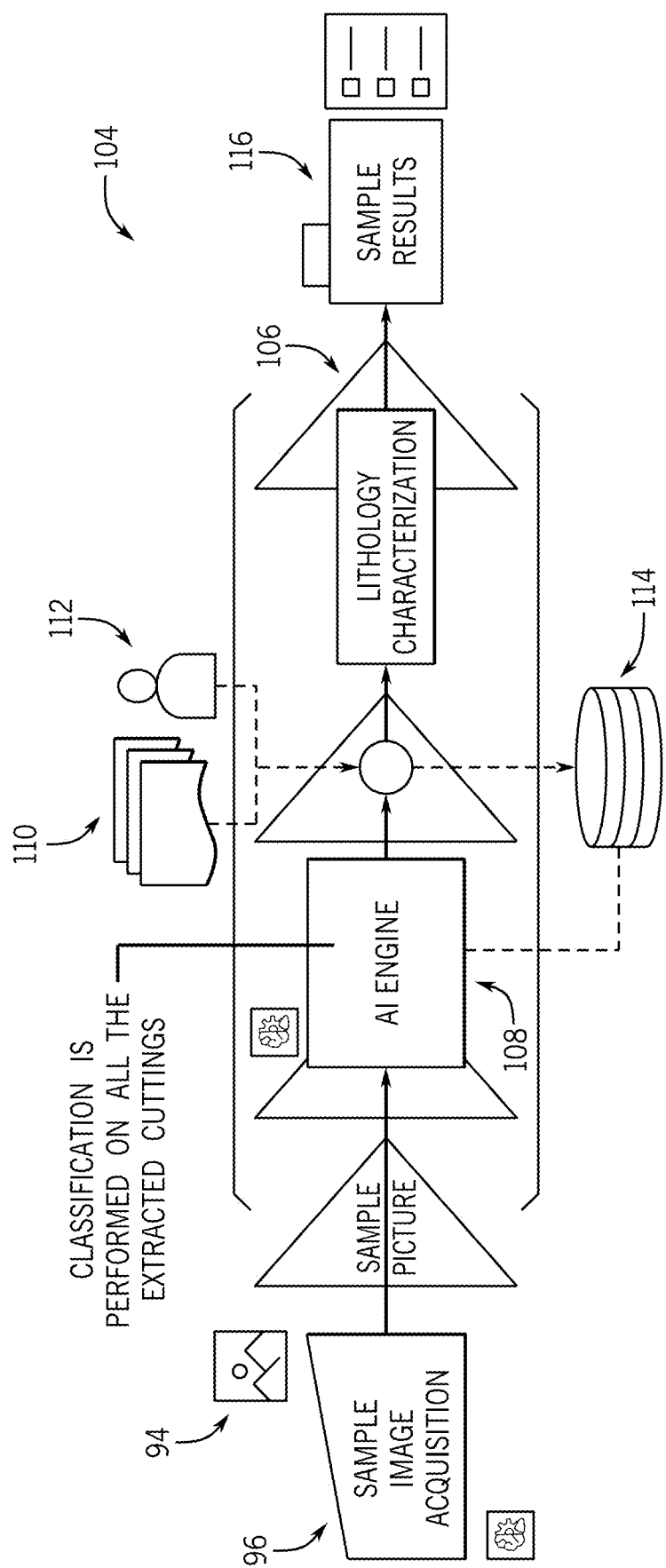
FIG. 6 illustrates an example workflow for lithological characterization of cuttings based on analysis of photos of the cuttings, in accordance with embodiments of the present disclosure.

Certain embodiments implement lithological recognition and/or classification from photos 94 of cuttings 46 by applying neural network (NN) and machine learning (ML) techniques. FIG. 6 illustrates an example workflow 104 for lithological characterization 106 of cuttings 46 based on analysis of photos 94 of the cuttings 46 using an artificial intelligence (AI) engine 108. In particular, as illustrated in FIG. 6, photos 94 of cuttings 46 may be analyzed by the AI engine 108 using, for example, certain AI algorithms 110, expert knowledge received from one or more operators 112, data stored in one or more databases 114, and other sources of algorithms and data, to perform the lithological characterization 106 to generate sample results 116, which may be used by the analysis and control system 50 to adjust operating parameters of a drilling operation 10, as described in greater detail herein.

However, as illustrated in FIG. 6, often, classification of the cuttings 46 is performed on all extracted cuttings 46, and not on an individual cutting level. In other words, characterization is often performed either based on a photo 94 as a whole or based on individual pixels within the photo 94. In addition, such classification of the cuttings 46 often are not based on quantitative photography acquisition or lithology physical characteristic measurements (e.g., color, grain size, texture, and so forth) that can be observed in a particular photo 94 of cuttings 46.

In contrast, the embodiments described herein apply object-based image analysis to focus the classification on an object of interest (e.g., depicted in a photo 94) where lithological information resides. Although the embodiments described herein are described mainly in terms of cutting image lithology recognition and measurements, the techniques described herein may also be extend to the analysis of images of outcrops (e.g., beds, laminate, heterogeneities, and so forth), cores (e.g., depending on the relative bed angles, and so forth, as long as the acquisition steps are performed under controlled conditions.

The embodiments described herein are distinguishable over conventional cutting recognition techniques that are based on semantic segmentation machine learning. For example, the embodiments described herein assess color accuracy and resolution against an intended application (i.e., quantitative photography). In addition, the embodiments described herein apply instance segmentation to extract individual cuttings 46 from a particular photo 94 (i.e., each individual cutting 46 is identified from a pile of cuttings 46 depicted in a particular photo 94). In other words, a plurality of individual pixels in a particular photo 94 that relate to a particular individual cutting 46 are identified as corresponding to that particular individual cutting 46, and may be analyzed together, as described in greater detail herein, to determine properties of the particular individual cutting 46. In addition, the embodiments described herein ascertain measurements of color distribution, grain size, size and shape (and other morphological properties), texture classification, and so forth, of individual cuttings 46 identified in photos 94. In addition, the embodiments described herein consolidate the results at the sample level with the possibility of analyzing at both the sample level as well as at the individual cutting level. It should be noted that while described primarily herein as ascertaining measurements of color distribution, grain size, size and shape, texture classification of individual cuttings 46 identified in photos 94, in other embodiments, other features of individual cuttings 46 may be identified in photos 94 by the analysis and control system 50.

As such, the embodiments described herein quantitatively assess and calibrate photos 94 of cuttings 46 for color accuracy and resolution, thereby providing a workflow that is more robust than conventional cutting recognition techniques with respect to accuracy, repeatability, and so forth. In addition, the embodiments described herein provide a workflow that is modular in nature, whereby each module may be improved and modified separately, thereby providing a high level of control. In addition, the embodiments described herein provide a workflow whereby the core measurements and analysis modules are tied to the geological definition of lithology. As such, by simply changing the instance segmentation, the workflow may be applied to a different type of lithology photographs (e.g., individual cuttings vs. cores vs. outcrops).

Figure 7:
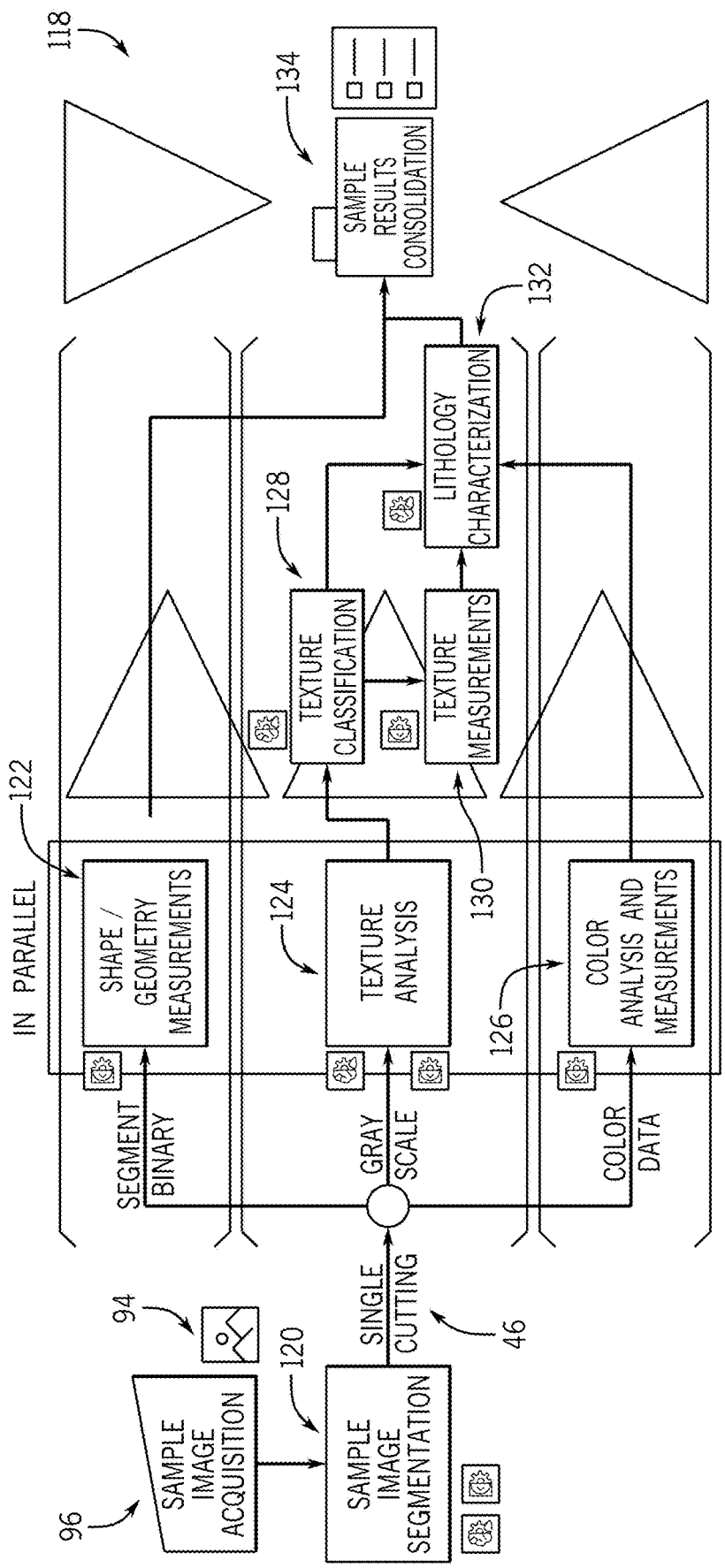
FIG. 7 illustrates another example workflow for lithological characterization of cuttings based on analysis of photos of the cuttings that improves upon the workflow of FIG. 6, in accordance with embodiments of the present disclosure.

FIG. 7 illustrates another example workflow 118 for lithological characterization of cuttings 46 based on analysis of photos 94 of the cuttings 46 that improves upon the workflow 104 described with respect to FIG. 6. In particular, as illustrated in FIG. 7, in certain embodiments, photos 94 of cuttings 46 may be first be analyzed by a sample image segmentation module 120 that identifies individual cuttings 46 depicted in the photos 94. Then, in certain embodiments, each individual cutting 46 (i.e., the portion of the corresponding photo 94 that includes the individual cutting) identified in the photos 94 are analyzed by three separate analysis modules in parallel: (1) a shape/geometry measurements module 122 that identifies shapes and geometries of each individual cutting 46, (2) a texture analysis module 124 that identifies textures of each individual cutting 46, and (3) a color analysis/measurements module 126 that identifies colors of each individual cutting 46.

Then, in certain embodiments, the identified texture data of each individual cutting 46 may be classified and measured by a texture classification module 128 and a texture measurements module 130, which feed these results into a lithology characterization module 132. In addition, in certain embodiments, the identified color data of each individual cutting 46 may also be fed into the lithology characterization module 132, which uses the texture classification and measurement data as well as the color data of each individual cutting 46 to perform the lithological characterization, the lithological characterization data from which may be consolidated with the shape and geometry data of each individual cutting 46 by a sample results consolidation module 134, the consolidated results data from which may be used by the analysis and control system 50 to adjust operating parameters of a drilling operation 10, as described in greater detail herein.

As such, in certain embodiments, the workflow 118 illustrated in FIG. 7 may include six phases, each phase of which may include one or more analysis modules: (1) calibrated and assessed photograph acquisition (e.g., of a particular photo 94 as performed by the photo acquisition module 96, and so forth); (2) sample image segmentation (e.g., as performed by the sample image segmentation module 120, and so forth); (3) cutting segment clustering/classification (e.g., morphological-based lithology identification at the cluster/class level); (4) quantitative measurements at the single cutting and cutting class level that include, but are not limited to, average color, texture type, main grain size and grain size distribution (if apply), shape and size parameters, and so forth (e.g., as performed by the shape/geometry measurements module 122, the texture analysis module 124, the color analysis/measurements module 126, the texture classification module 128, the texture measurements module 130, the lithology characterization module 132, and so forth); (5) report consolidation of the sample (e.g., of the particular photo 94 as performed by the sample results consolidation module 134); and (6) final preparation of a mudlog, and so forth, based on the consolidated report data. Because of the modularity of the object-based cutting image analysis workflow 118 illustrated in FIG. 7, the embodiments described herein are configured to facilitate the use of any particular analysis modules that are desired in view of the particular drilling operation 10 and its associated operational parameters to obtain mid-final results.

Figure 8A:
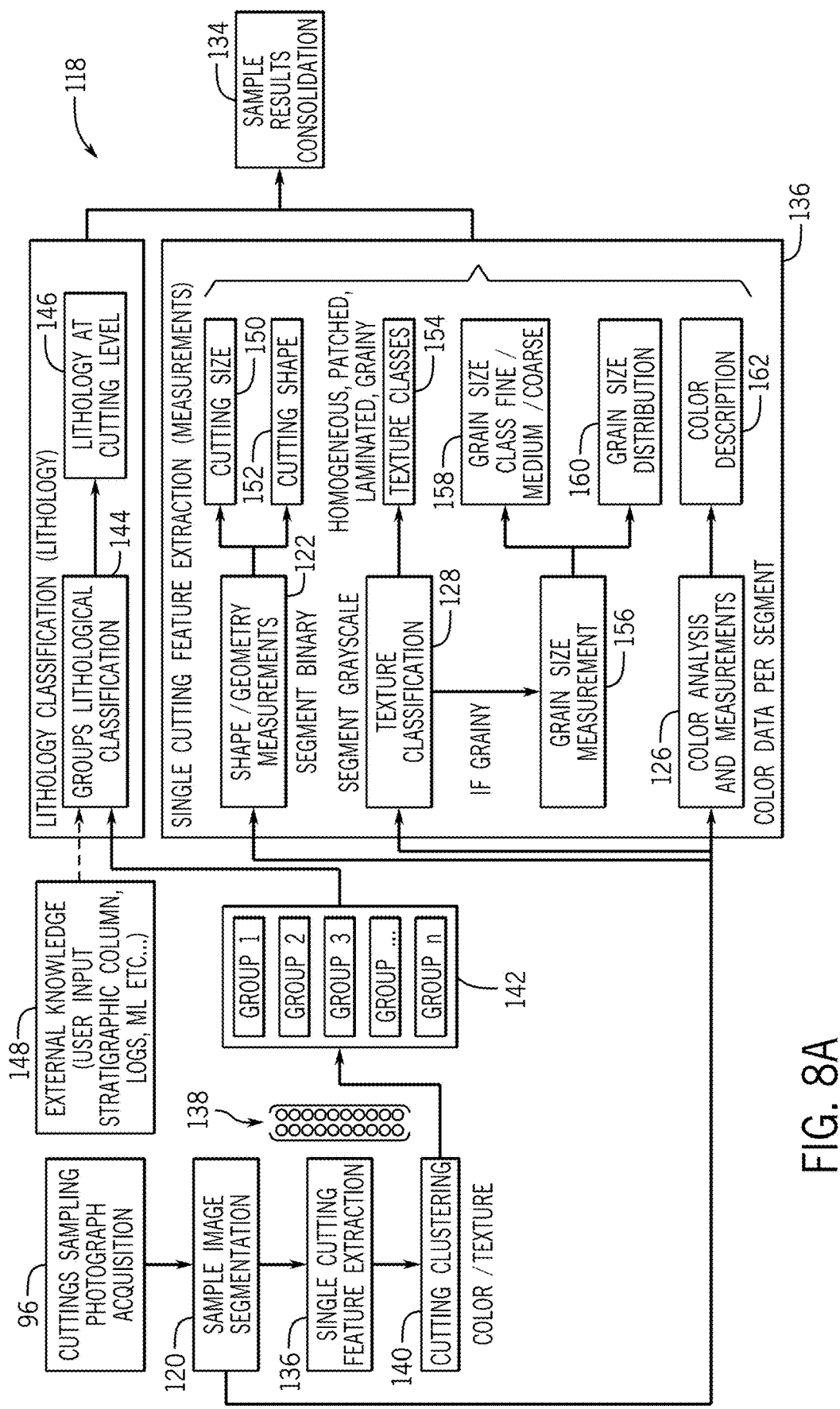
FIGS. 8A and 8B illustrate other embodiments of the object-based cutting image analysis workflow of FIG. 7, in accordance with embodiments of the present disclosure.
Figure 8B:
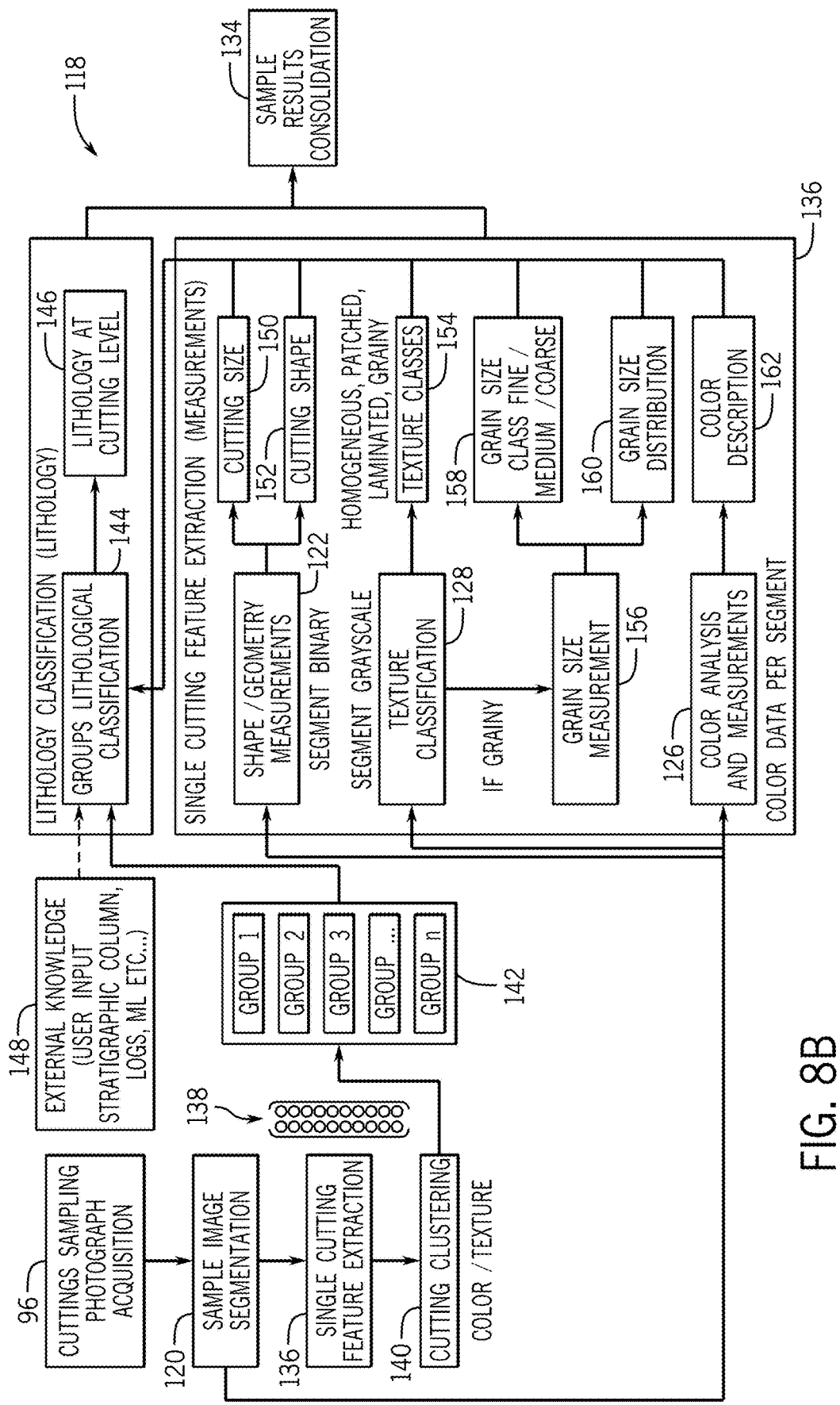

FIGS. 8A and 8B illustrate other embodiments of the object-based cutting image analysis workflow 118 of FIG. 7. For example, as illustrated in FIG. 8A, in certain embodiments, a single cutting feature extraction module 136 may work in conjunction with the sample image segmentation module 120 to extract single cutting features 138 of the individual cuttings 46 directly from instances of photos 94, and a cutting/clustering module 140 may be used to identify clusters of individual cuttings 46 that may be grouped together into groups 142 of cuttings 46 that have similar cutting features. Then, in certain embodiments, the groups 142 of cuttings 46 may be analyzed by a groups lithological classification module 144 to determine the lithology 146 of each group 142 of cuttings 46 at the cutting level. In certain embodiments, the groups lithological classification module 144 may also take into account external knowledge (e.g., user inputs, stratigraphic column data, log data, machine learning data, and so forth) to determine the lithology 146 of each group 142 of cuttings 46 at the cutting level. In certain embodiments, the groups lithological classification module 144 may also be configured to perform the lithological classification by using external data 148 such as, but not limited to, stratigraphic geological sequences, while-drilling logs, 3D model properties, cutting physical analysis such as diffractometry, or any other information that may be useful to resolve lithology classification ambiguities. In addition, in certain embodiments, the groups lithological classification module 144 may also be configured to perform the lithological classification by using image physics of, for example, ultraviolet images, infrared images, near-infrared images, or some combination thereof.

As illustrated in more detail, the single cutting feature extraction module 136 may analyze the individual cuttings 46 identified by the sample image segmentation module 120 using, among other analysis modules: (1) the shape/geometry measurements module 122 that identifies a cutting size 150 and a cutting shape 152, among other shape/geometrical properties, of each individual cutting 46; (2) the texture classification module 128 that classifies each individual cutting 46 to identify various texture classes 154 (e.g., homogeneous, patched, laminated, grainy, and so forth) of each individual cutting 46; (3) a grain size measurement module 156 that analyses each individual cutting 46 to identify a grain size class (e.g., fine, medium, coarse, and so forth) 158 and a grain size distribution 160, among other grain size-related properties, of each individual cutting 46; and (4) the color analysis/measurements module 126 that identifies a color description 162, among other color-related properties, of each individual cutting 46.

FIG. 8B illustrates an alternative embodiment where the lithological classification performed by the groups lithological classification module 144 is performed based on the morphological, color, texture, grain size, and grain distribution data extracted by the single cutting feature extraction module 136, as opposed to being performed by the groups lithological classification module 144 based on features 138 directly extracted from the individual cuttings 46 that represent the morphological, color, texture, grain size, and grain distribution data, such as in the embodiment illustrated in FIG. 8A. Again, although illustrated in FIGS. 8A and 8B as ascertaining measurements of color, texture type, grain size and grain size distribution, and shape and size parameters of individual cuttings 46 identified in photos 94, in other embodiments, other features of individual cuttings 46 may be identified in photos 94 by the analysis and control system 50.

Figure 9:
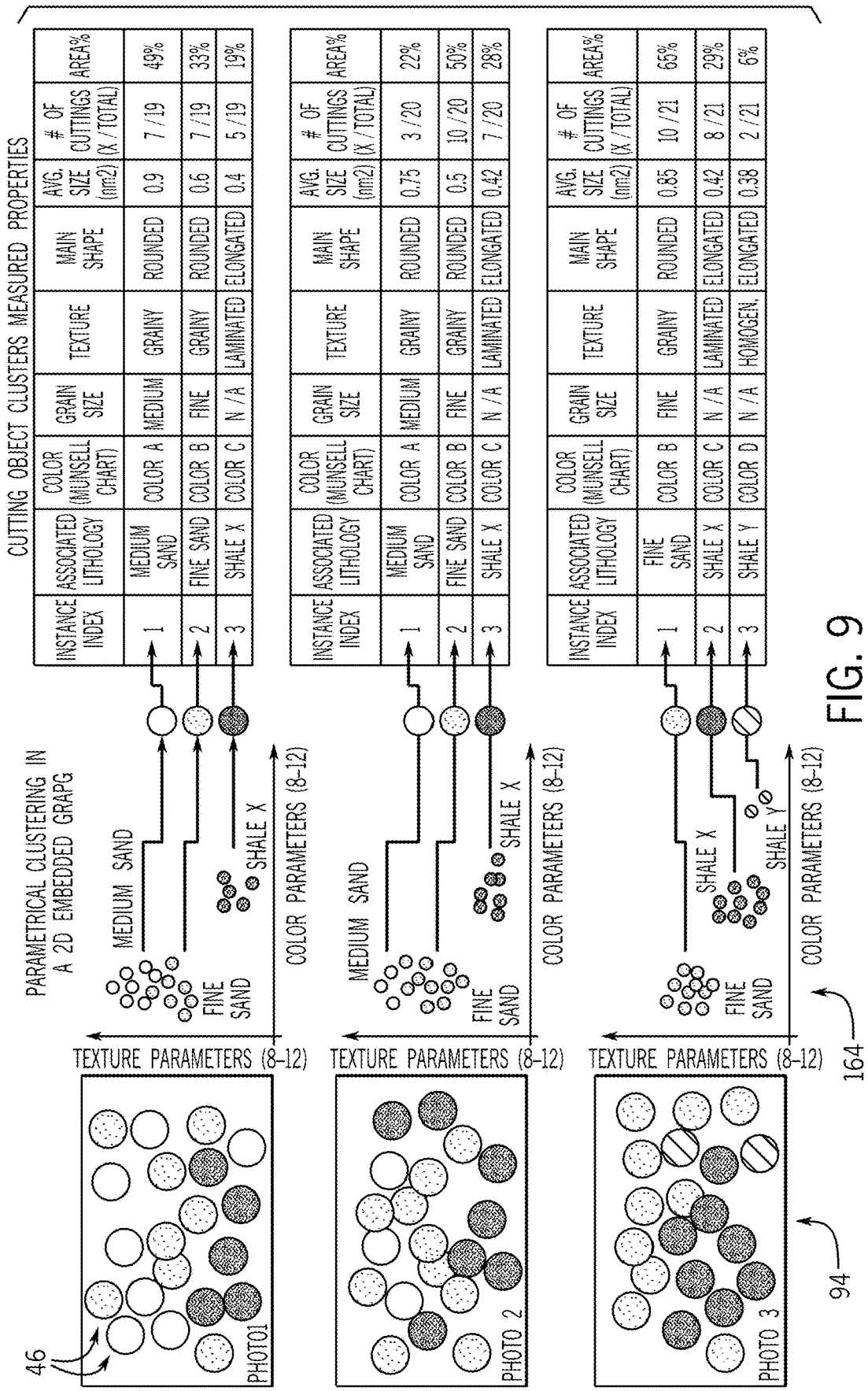
FIG. 9 illustrates how the object-based image analysis and quantitative photographic acquisition of the workflow illustrated in FIGS. 7 and 8 enable detailed characterization of each instance class recognized in a photograph, in accordance with embodiments of the present disclosure.

FIG. 9 illustrates how the object-based image analysis and quantitative photographic acquisition of the workflow 118 illustrated in FIGS. 7 and 8 enable detailed characterization of each instance class recognized in a photograph 94. Specifically, FIG. 9 illustrates how color and texture parameters may be synthetized in a two-dimensional plot 164 (e.g., of lithology vs. texture) and used for the lithology classification and quantitative characterization described with respect to FIGS. 7 and 8. In particular, in the example illustrated in FIG. 9, three photographs 94 that include four different lithologies of cuttings 46 (e.g., fine sand, medium sand, shale X, and shale Y, as represented by the shading (i.e., color) of the cuttings 46) having various textures (e.g., grainy, laminated, and homogeneous, as represented by the dots and dashes of the cuttings 46) are being analyzed. In addition, as illustrated in FIG. 9, in certain embodiments, for each photograph 94, each group of cuttings 46 having similar lithologies may have the individual cuttings 46 in the group counted relative to all of the cuttings 46 identified in the photograph 94 with the main shape (e.g., rounded, elongated, and so forth), average size, and percentage of area (e.g., the relative total of cutting count times average size) of each group of cuttings 46 may be determined. An automated cutting description is, therefore, possible with objective measurements with relatively high precision using the object-based image analysis and quantitative photographic acquisition of the workflow 118. The example illustrated in FIG. 9 shows how the clustering phase makes it possible to set boundaries, even between clusters that are gradually changing (e.g., fine-medium sand).

Figure 10:
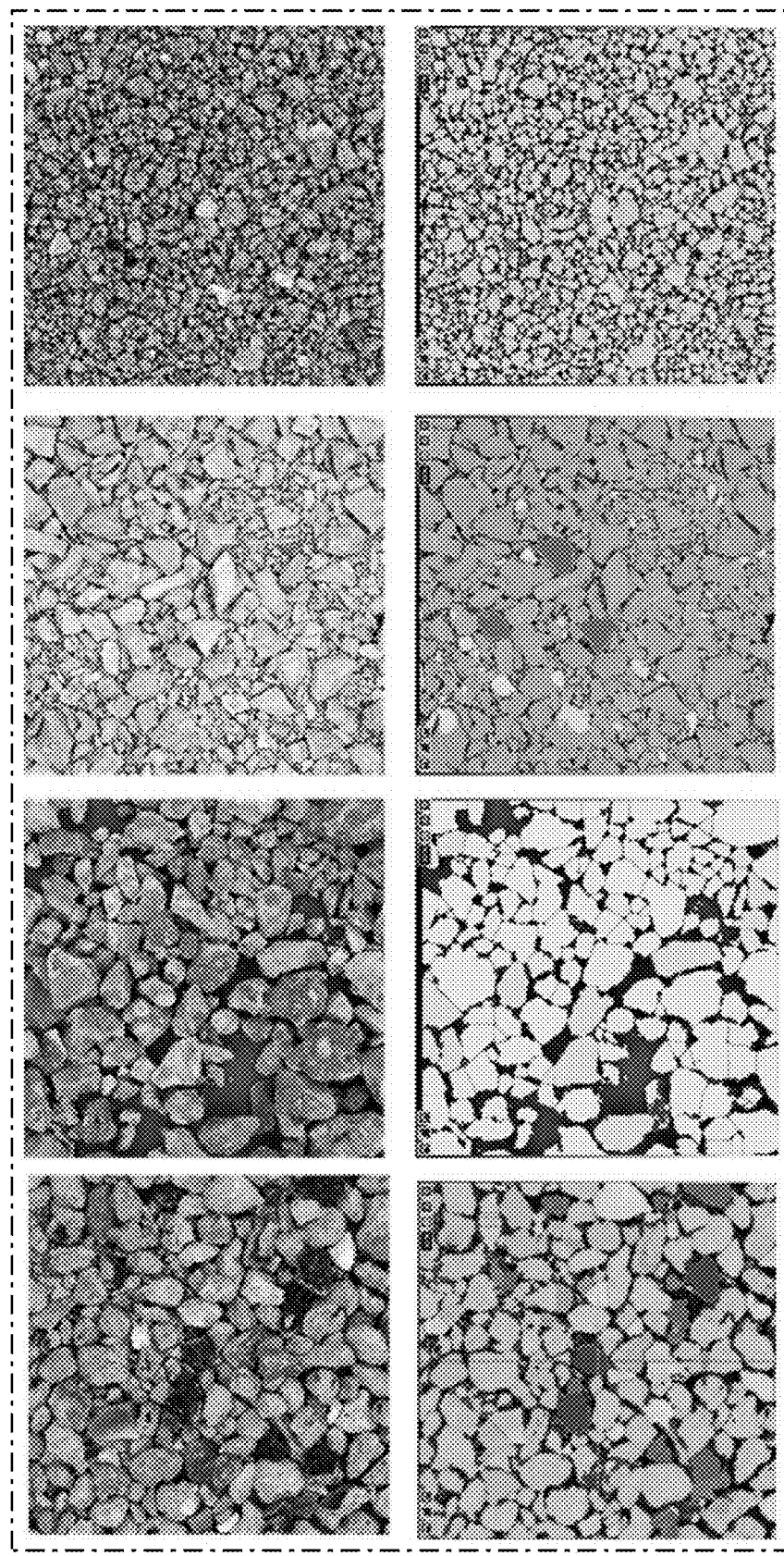
FIG. 10 illustrates examples of single cutting based classification that considers color, texture, and grain size, among other parameters, of individual cuttings identified in various photographs, in accordance with embodiments of the present disclosure.
Figure 11:
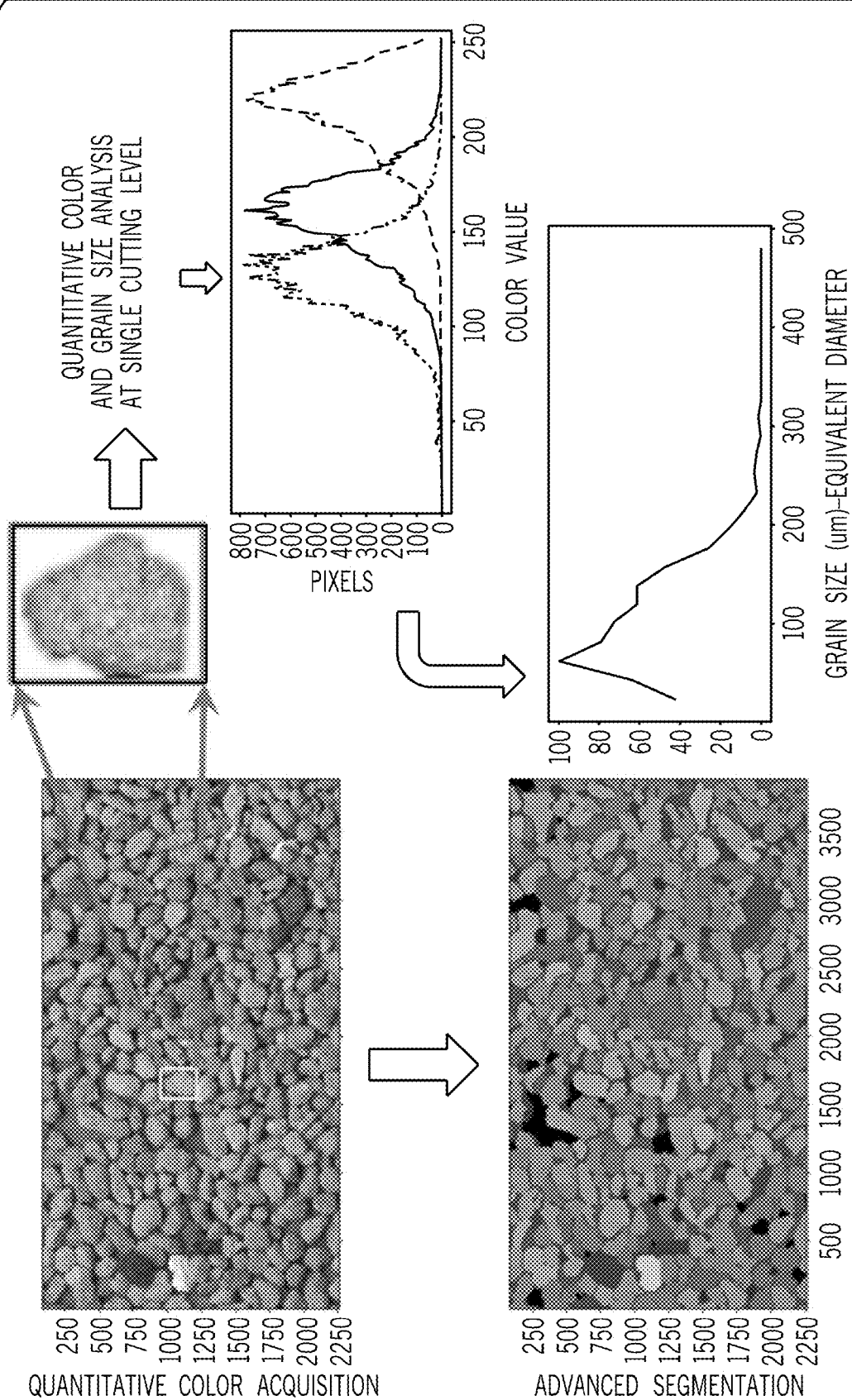
FIG. 11 illustrates an example of cutting segmentation results along with color and grain size measurements that can be consolidated at the sample level, in accordance with embodiments of the present disclosure.

FIG. 10 illustrates examples of the single cutting based classification that considers color, texture, and grain size, among other parameters, of individual cuttings 46 identified in various photographs 94, as described in greater detail herein. In addition, FIG. 11 illustrates an example of cutting segmentation results along with color and grain size measurements that can be consolidated at the sample level and used for relatively basic analysis (e.g., automated cutting description, as represented by the top row) or relatively advanced (e.g., drilling, petrophysics, geology, and other operations).

As such, in certain embodiments, the analysis and control system 50 is configured to separate pixels of individual rock particles from multiple particles (e.g., cuttings 46) depicted in a calibrated photograph 94. In addition, in certain embodiments, the analysis and control system 50 is configured to extract relevant feature data relating to one or more features of one or more individual rock particles (e.g., cuttings 46) depicted in a calibrated photograph 94. In addition, in certain embodiments, the analysis and control system 50 is configured to utilize extracted information from calibrated photographs 94 to perform geological/lithological classification at a plurality of different hierarchical levels (e.g., at a single particle/cutting level, at a single sample level of a plurality of cuttings, at a particular depth interval within a borehole 22, for a particular geological formation 24, for an entire well, for an entire well field, and so forth). As described in greater detail herein, consolidating the analysis results in a plurality of hierarchical levels enables operators to analyze the cuttings 46 in a much more robust (and automated and more accurate) manner than conventional techniques. In addition, in certain embodiments, the analysis and control system 50 is configured to utilize the information derived herein based on the calibrated photographs 94 to create a mud logging report. In addition, in certain embodiments, the analysis and control system 50 is configured to output from the calibrated photographs 94 any relevant information that can be integrated with other well-related answer products. In addition, in certain embodiments, the analysis and control system 50 is configured to utilize a supervised machine learning model (e.g., from another well in the same field or another field with similar geological setting) to infer the lithology type from a photograph 94 from the current well.

In addition, in certain embodiments, the analysis and control system 50 is configured to extracts features of each instance of individual cutting 46 with techniques such as image textural filters (e.g., Gabor filters, and so forth), an autoencoder, or other deep learning based techniques. In addition, in certain embodiments, the analysis and control system 50 is configured to embed and display cuttings 46 in a two-dimensional (2D) or three-dimensional (3D) map 164 (or, even a multi-dimensional map having more than three dimensions) using extracted features, and further compress features using techniques such as t-distributed stochastic neighbor embedding (t-SNE), principal component analysis (PCA), and so forth. In certain embodiments, one or more of the axes of the map 164 may be a color property, and one or more of the other axes may be a texture property. In addition, in certain embodiments, all of the axes of the map 164 may be a mix of color and texture properties. In addition, in certain embodiments, the analysis and control system 50 is configured to enable users to annotate lithology type for each cutting 46 in the 2D or 3D map 164 via a user interface displayed on a display 80 of the analysis and control system 50. In addition, in certain embodiments, the analysis and control system 50 is configured to group the cuttings 46 from one or more image 94 based on the extracted features using a clustering technique, such as k-means, to facilitate the user annotation.

In addition, in certain embodiments, the analysis and control system 50 is configured to create a relatively light-weight supervised machine learning model based on the extracted features and the user annotation of lithology type, which takes an individual instance of a cutting 46 as an input a lithology type as an output. In addition, in certain embodiments, the analysis and control system 50 is configured to infer the lithology type when a new photo 94 is obtained using the trained supervised machine learning model. In certain embodiments, when the inference of the lithology is not satisfactory, a user may modify the annotation via a graphical user interface, and the model may be retrained. The workflow 118 offers this dynamic (or active) model improvement experience. By this process, the model is expected to improve to better predict the lithology of a well being analyzed. Instead of creating a model from scratch, the default global model (e.g., trained with typical lithology data) may be provided as part of the software, and a user may update this global model by retraining the model with the data and annotations from the data that the user is analyzing.

In addition, in certain embodiments, the analysis and control system 50 is configured to extract features from an image 94 of cuttings 46 and classify the cuttings 46 into geological texture categories, such as homogeneous, heterogeneous, laminated, grainy, and so forth. In certain embodiments, the grainy texture category may further be classified into fine/medium/coarse categories. In certain embodiments, for the classification technique, features based on local binary patterns and thresholds on those properties, or convolutional neural networks, may be used by the analysis and control system 50. In addition, in certain embodiments, the analysis and control system 50 is configured to use the categories (e.g., fine/medium/coarse) of grainy cuttings 46 to set parameters of the cuttings distribution analysis. In addition, in certain embodiments, the texture classification described herein may be expanded to other, more complex textures based on actual geological classifications, such as the Folk and Duncan carbonate classifications, the six classes igneous texture classification (e.g., phaneritic, aphanitic, porphyritic, glassy, pyroclastic, and pegmatitic), and so forth, as but a few non-limiting examples.

Figure 12:
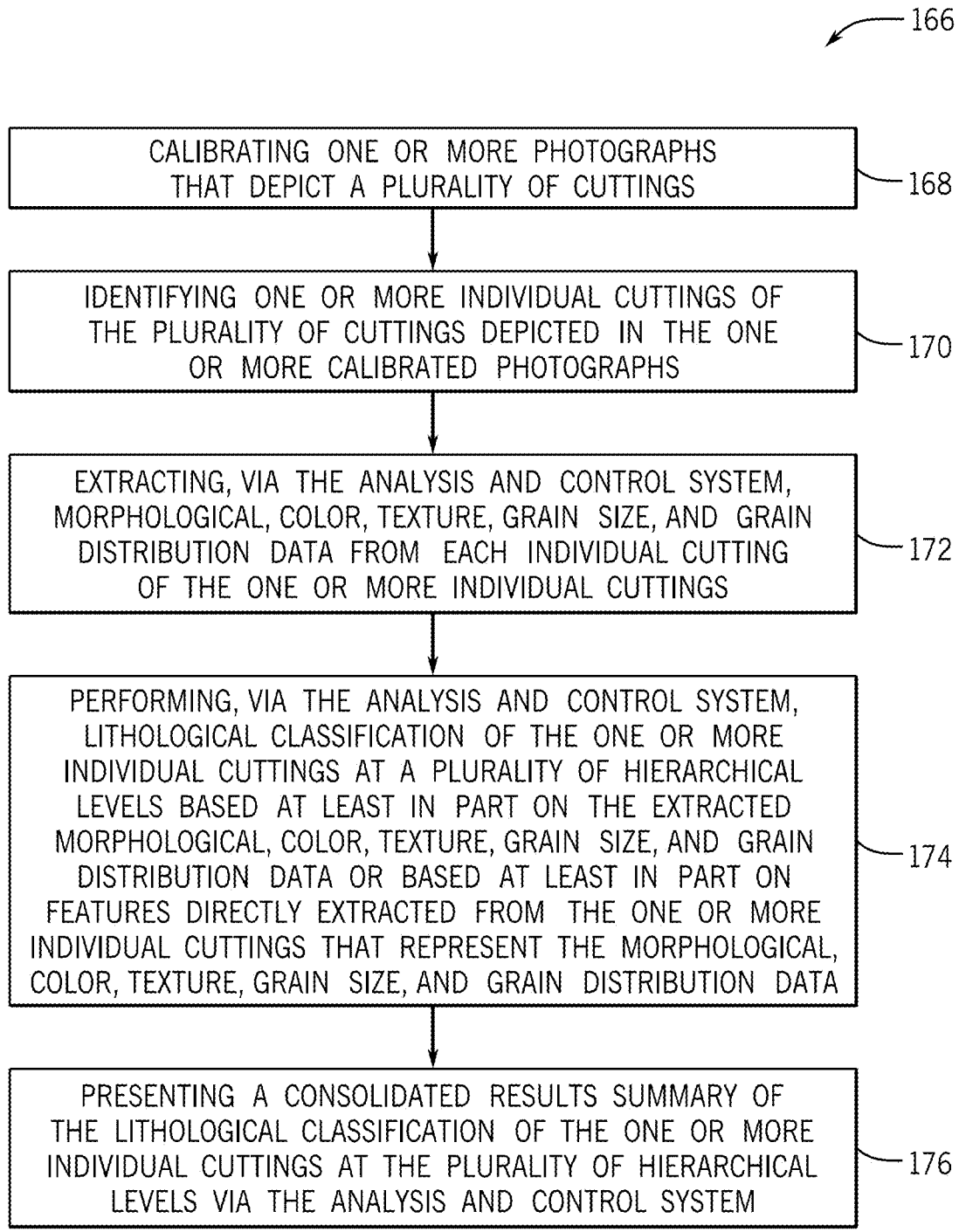
FIG. 12 is a flow diagram of a method of using the analysis and control system of FIG. 4, in accordance with embodiments of the present disclosure.

FIG. 12 is a flow diagram of a method 166 of using the analysis and control system 50 of FIG. 4, as described in greater detail herein. As illustrated, in certain embodiments, the method 166 may include calibrating, via the analysis and control system 50, one or more photographs 94 that depict a plurality of cuttings 46 (block 168). In addition, in certain embodiments, the method 166 may include identifying, via the analysis and control system 50, one or more individual cuttings 46 of the plurality of cuttings 46 depicted in the one or more calibrated photographs 94 (block 170). In addition, in certain embodiments, the method 166 may include extracting, via the analysis and control system 50, morphological, color, texture, grain size, and grain distribution data from each individual cutting 46 of the one or more individual cuttings 46 (block 172). In addition, in certain embodiments, the method 166 may include performing, via the analysis and control system 50, lithological classification of the one or more individual cuttings 46 at a plurality of hierarchical levels based at least in part on the extracted morphological, color, texture, grain size, and grain distribution data or based at least in part on features directly extracted from the one or more individual cuttings that represent the morphological, color, texture, grain size, and grain distribution data (block 174). In addition, in certain embodiments, the method 166 may include presenting, via the analysis and control system 50, a consolidated results summary of the lithological classification of the one or more individual cuttings 46 at the plurality of hierarchical levels via the analysis and control system 50 (block 176). Although described primarily herein as extracting morphological, color, texture, grain size, and grain distribution data, and using such data to lithologically classify the one or more individual cuttings 46, in other embodiments, any and all subsets of the morphological, color, texture, grain size, and grain distribution data may be extracted and used to lithologically classify the one or more individual cuttings 46.

In addition, in certain embodiments, the method 166 may include calibrating, via the analysis and control system 50, the one or more photographs with one or more previously analyzed photographs 94 with respect to color, illumination, and resolution. In addition, in certain embodiments, the method 166 may include retraining, via the analysis and control system 50, a lithological classification model (e.g., as performed by the groups lithological classification module 144) based at least in part on one or more annotations added by a user of the analysis and control system 50. In addition, in certain embodiments, the lithological classification is based at least in part on stratigraphic geological sequences, while-drilling logs, 3D model properties, cutting physical analysis such as diffractometry, ultraviolet images, infrared images, near-infrared images, or some combination thereof.

In addition, in certain embodiments, the method 166 may include automatically adjusting, via the analysis and control system 50, one or more operating parameters of a drilling operation 10 from which the plurality of cuttings 46 were generated based at least in part on the lithological classification of the one or more individual cuttings 46. In addition, in certain embodiments, the method 166 may include generating, via the analysis and control system 50, a mud logging report based at least in part on the lithological classification of the one or more individual cuttings 46. In addition, in certain embodiments, identifying the one or more individual cuttings 46 may include identifying a set of pixels in the one or more calibrated photographs 94 that correspond to each individual cutting 46 of the one or more individual cuttings 46. In addition, in certain embodiments, the plurality of hierarchical levels include some combination of: an individual cutting level, a sample level, a particular depth interval within a borehole, a geological formation level, a well level, and a well field level.

In addition, in certain embodiments, identifying the one or more individual cuttings 46 of the plurality of cuttings 46 depicted in the one or more calibrated photographs 94 may include extracting a plurality of features of each individual cutting 46 of the one or more individual cuttings 46. In certain embodiments, the plurality of features may include a color and a texture of each individual cutting 46 of the one or more individual cuttings 46. In addition, in certain embodiments, the method 166 may include grouping, via the analysis and control system 50, the plurality of cuttings 46 into subsets of the plurality of cuttings 46 based on shared features among the subsets of the plurality of cuttings 46. In addition, in certain embodiments, the method 166 may include displaying, via a display of the analysis and control system 50, the plurality of cuttings 46 in a multi-dimensional map 164, wherein each axis of the multi-dimensional map 164 corresponds to a feature of the plurality of features. In addition, in certain embodiments, the method 166 may include enabling, via the analysis and control system 50, a user to annotate the lithological classification of one or more individual cuttings 46 on the multi-dimensional map 164.

The specific embodiments described above have been illustrated by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

In the claims, means-plus-function clauses are intended to cover the structures described herein as performing the recited function and not only structural equivalents, but also equivalent structures. Thus, for example, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words "means for" together with an associated function.

The invention claimed is:

1. A method, comprising:
calibrating, via an analysis and control system, one or more photographs that depict a plurality of cuttings;
identifying, via the analysis and control system, one or more individual cuttings of the plurality of cuttings depicted in the one or more calibrated photographs;
extracting, via the analysis and control system, morphological, color, texture, grain size, and grain distribution data from each individual cutting of the one or more individual cuttings;
performing, via the analysis and control system, lithological classification of the one or more individual cuttings at a plurality of hierarchical levels based at least in part on the extracted morphological, color, texture, grain size, and grain distribution data; and
presenting, via the analysis and control system, a consolidated results summary of the lithological classification of the one or more individual cuttings at the plurality of hierarchical levels via the analysis and control system.

2. The method of claim 1, comprising automatically adjusting, via the analysis and control system, one or more operating parameters of a drilling operation from which the plurality of cuttings were generated based at least in part on the lithological classification of the one or more individual cuttings.

3. The method of claim 1, wherein calibrating, via the analysis and control system, the one or more photographs comprises calibrating the one or more photographs with one or more previously analyzed photographs with respect to color, illumination, and resolution.

4. The method of claim 1, comprising retraining, via the analysis and control system, a lithological classification model based at least in part on one or more annotations added by a user of the analysis and control system.

5. The method of claim 1, wherein the lithological classification is based at least in part on stratigraphic geological sequences, while-drilling logs, 3D model properties, cutting physical analysis, ultraviolet images, infrared images, near-infrared images, or some combination thereof.

6. The method of claim 1, wherein identifying the one or more individual cuttings comprises identifying a set of pixels in the one or more calibrated photographs that correspond to each individual cutting of the one or more individual cuttings.

7. The method of claim 1, wherein the plurality of hierarchical levels comprises some combination of: an individual cutting level, a sample level, a particular depth interval within a borehole, a geological formation level, a well level, and a well field level.

8. The method of claim 1, wherein identifying the one or more individual cuttings of the plurality of cuttings depicted in the one or more calibrated photographs comprises extracting a plurality of features of each individual cutting of the one or more individual cuttings, and wherein the plurality of features comprises a color and a texture of each individual cutting of the one or more individual cuttings.

9. The method of claim 8, comprising:
grouping, via the analysis and control system, the plurality of cuttings into subsets of the plurality of cuttings based on shared features among the subsets of the plurality of cuttings; and
performing, via the analysis and control system, lithological classification of the subsets of the plurality of cuttings at the plurality of hierarchical levels based at least in part on the plurality of features extracted from the one or more individual cuttings.

10. The method of claim 8, comprising:
displaying, via a display of the analysis and control system, the plurality of cuttings in a multi-dimensional map, wherein each axis of the multi-dimensional map corresponds to a feature of the plurality of features; and
enabling, via the analysis and control system, a user to annotate the lithological classification of one or more individual cuttings on the multi-dimensional map.

11. An analysis and control system configured to:
calibrate one or more photographs that depict a plurality of cuttings;
identify one or more individual cuttings of the plurality of cuttings depicted in the one or more calibrated photographs;
extract morphological, color, texture, grain size, and grain distribution data from each individual cutting of the one or more individual cuttings;
perform lithological classification of the one or more individual cuttings at a plurality of hierarchical levels based at least in part on the extracted morphological, color, texture, grain size, and grain distribution data; and
present a consolidated results summary of the lithological classification of the one or more individual cuttings at the plurality of hierarchical levels via the analysis and control system.

12. The analysis and control system of claim 11, wherein the analysis and control system is configured to automatically adjust one or more operating parameters of a drilling operation from which the plurality of cuttings were generated based at least in part on the lithological classification of the one or more individual cuttings.

13. The analysis and control system of claim 11, wherein the analysis and control system is configured to calibrate the one or more photographs with one or more previously analyzed photographs with respect to color, illumination, and resolution.

14. The analysis and control system of claim 11, wherein the analysis and control system is configured to retrain a lithological classification model based at least in part on one or more annotations added by a user of the analysis and control system.

15. The analysis and control system of claim 11, wherein the lithological classification is based at least in part on stratigraphic geological sequences, while-drilling logs, 3D model properties, cutting physical analysis, ultraviolet images, infrared images, near-infrared images, or some combination thereof.

16. The analysis and control system of claim 11, wherein identifying the one or more individual cuttings comprises identifying a set of pixels in the one or more calibrated photographs that correspond to each individual cutting of the one or more individual cuttings.

17. The analysis and control system of claim 11, wherein the plurality of hierarchical levels comprises some combination of: an individual cutting level, a sample level, a particular depth interval within a borehole, a geological formation level, a well level, and a well field level.

18. The analysis and control system of claim 11, wherein identifying the one or more individual cuttings of the plurality of cuttings depicted in the one or more calibrated photographs comprises extracting a plurality of features of each individual cutting of the one or more individual cuttings, and wherein the plurality of features comprises a color and a texture of each individual cutting of the one or more individual cuttings.

19. The analysis and control system of claim 18, wherein the analysis and control system is configured to:
group the plurality of cuttings into subsets of the plurality of cuttings based on shared features among the subsets of the plurality of cuttings; and
perform lithological classification of the subsets of the plurality of cuttings at the plurality of hierarchical levels based at least in part on the plurality of features extracted from the one or more individual cuttings.

20. The analysis and control system of claim 18, wherein the analysis and control system is configured to:
display the plurality of cuttings in a multi-dimensional map, wherein each axis of the multi-dimensional map corresponds to a feature of the plurality of features; and
enable a user to annotate the lithological classification of one or more individual cuttings on the multi-dimensional map.

* * * * *